United States Patent
Paulasaari et al.

(10) Patent No.: US 6,291,623 B1
(45) Date of Patent: Sep. 18, 2001

(54) FLUOROALKYLSUBSTITUTED CYCLOTRISILOXANES, THEIR USE FOR PREPARATION OF NEW POLYMERS AND NOVEL POLYMERS

(75) Inventors: Jyri Kalevi Paulasaari; William P. Weber, both of Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/416,266

(22) Filed: Oct. 12, 1999

(51) Int. Cl.[7] .................................................. C08G 77/24
(52) U.S. Cl. .............................. 528/42; 528/25; 556/448; 556/454; 556/479
(58) Field of Search ...................... 528/25, 42; 556/448, 556/454, 479

(56) References Cited

U.S. PATENT DOCUMENTS

3,070,617  * 12/1962  Holbrook .
3,364,244     1/1968  Selin ................................. 260/448.2
5,350,824  *  9/1994  Kobayashi .

OTHER PUBLICATIONS

Jyri K. Paulasaari and William P. Weber, "Preparation and polymerization of 1,3,3,5,5-pentamethyl-1-(2'-perfluorophenyl-1',1',2',2'-tetrahydroethyl)cyclostrisiloxane (I). Comparison of anionic and cationic polymerization of I", 39 Polym. Prepr., 583–584 (1998) (Abstract).

Jyri K. Paulasaari and William P. Weber, "Preparation and Orthogonal Polymerizations of 1–Hydrido–1–vinyldimethylsiloxy–3,3,5,5-tetramethylcyclotrisiloxane", 32 Macromolecules 5217–5221 (1999) (Abstract).

Jyri K. Paulasaari and William P. Weber, "Polymerization of 1–Hydrido–1–vinyldimethylsiloxy–3,3,5,5-tetramethylcyclotrisiloxane", 40 Polym. Prepr. 801–802 (1999) (Abstract).

Jyri K. Paulasaari and William P. Weber, "Preparation of Highly Regular Poly(1–Hydrido–1,3,3,5,5–pentamethyltrisiloxane) and Its Chemical Modification by Hydroxsilylation", 32 Macromolecules 6574–6577 (1999) (Abstract).

Rozga–Wijas et al., "Controlled Synthesis of Siloxane Copolymers Having an Organosulfur Group by Polymerization of Cyclotrisiloxanes with Mixed Units", 29 Macromolecules, 2711–2720 (1996).

Vasilenko et al., "Hyperbranched H–functional polydimethylsiloxanes based on macromonomers", STN International, File CAPLUS, Accession No. 1998: 142499, Book of Abstracts, 215th ACS National Meeting, Dallas, Mar. 29–Apr. 2(1998) POLY–254 Publisher: American Chemical Society, Washington, DC.

Vasilenko et al., "Organosilicon dendrimers and star–shaped polymers and block–co–polymers based on", 39 Polymer Preprints, 479–480 (1998).

Paulasaari et al., "Base catalyzed proton transfer polymerization of 1–hydroxypenta–methylcyclotrisiloxane. Comparison of hyperbranched polymer microstructure and properties to those of highly regular linear analogs", 201 Macromol. Chem. Phys., 1585–1592 (2000).

Paulasaari et al., "Synthesis of Hyperbranched Polysiloxanes by Base–Catalyzed Proton–Transfer Polymerization. Comparison of Hyperbranched Polymer Microstructure and Properties to Those of Linear Analogues Prepared by Cationic or Anionic Ring–Opening Polymerization", Macromolecules, 2005–2010 (2000).

Paulasaari et al., "Superbase Catalyzed Proton Transfer Polymerization of 1–(Hydroxydimethylsiloxy) pentamethylcyclotrisiloxane", 41 Polymer Preprints, 171–172 (2000).

Weber et al., "Synthesis and Properties of Poly(siloxanes) with Novel Architectures", 41 Polymer Preprints, 562–563 (2000).

Paulasaari et al., "Hyperbranched Polysiloxane via Base Catalyzed Proton Transfer Polymerization (PTP) of 1–Hydroxypentamethylcyclotrisiloxane", 41 Polymer Preprints, 159–160 (2000).

Guo Ping Cai et al., "Synthesis of Polymethyl(trimethylsiloxy) siloxane by Anionic Ring–Opening Polymerization of 1,3,5–Trimethyl–1,3,5–tris(trimethylsiloxy)cyclotrisiloxane", 33 Macromolecules, 6310–6314 (2000).

* cited by examiner

Primary Examiner—Robert Dawson
Assistant Examiner—Marc S. Zimmer
(74) Attorney, Agent, or Firm—James C. Lydon

(57) ABSTRACT

This invention relates to new fluoroalkyl substituted cyclotrisiloxanes, their use in the preparation of new homopolymers, block copolymers and random copolymers, and to such new homopolymers, block copolymers and random copolymers.

12 Claims, No Drawings

FLUOROALKYLSUBSTITUTED CYCLOTRISILOXANES, THEIR USE FOR PREPARATION OF NEW POLYMERS AND NOVEL POLYMERS

This invention concerns new fluoroalkylsubstituted cyclotrisiloxanes, new homopolymers and block coplymers derived from said cyclotrisiloxanes, and their preparation.

BACKGROUND OF THE INVENTION

The publications and other materials used herein to illuminate the background of the invention, and in particular, cases to provide additional details with respect to the practice, are incorporated by reference.

The only commercially available fluoroalkylsiloxane is poly(trifluoropropylmethylsiloxane). It is prepared via anionic or cationic ring opening polymerization of cyclotri (trifluoropropylmethylsiloxane). Crystalline fluoroalkylmethylpolysiloxane has been obtained from the monomer of pure cis-isomer.[1,2] Precursor of cyclotri (trifluoropropylmethylsiloxane) is trifluoropropylmethyldichlorosilane, prepared usually by platinum ($H_2PtCl_6$) catalyzed hydrosilation reaction between methyldichlorosilane and 3,3,3-trifluoropropene.[3] The reaction has also been applied to the preparation of bis(trifluoropropyl)dichlorosilane using dichlorosilane instead of methyldichlorosilane. Unlike non-fluorinated alkenes (ethene, propene) which give good yields between 60 and 79%,[4] 3,3,3-trifluoropropene gives only low yields, 26 . . . 36% in preparation of disubstituted silicon.[5] Bis (1H, 1H, 2H-perfluorohexyl)dichlorosiloxane has been obtained in 42% overall yield via a two step process, where both $Co_2(CO)_8$ and platinium cyclovinylmethylsiloxane complex were used for the hydrosilylation reaction between dichlorosilane and 1H, 1H, 2H-perfluorohexane.[6] High yields have been obtained via UV-light catalyzed radical reaction,[7,8,9]

3-(Pentafluorophenyl)ethylmethyldichlorosilane has been prepared in 70% yield from methyldichlorosilane and pentafluorostyrene.[10] Cyclics having both dimethylsiloxy and 3-(pentafluorphenyl)ethylmethylsiloxane units were prepared by Matsui et al[11] via hydrosilation reaction between pentafluorostyrene and cyclics containing dimethylsiloxy and methylsiloxy units. Polymerization of these cyclic was catalyzed by tetramethylammonium hydroxide, polymer $M_w/M_n$=38,000/21,000 g/mol. See Scheme 1.

Matsui also prepared hetero cyclics of dimethyldichlorosilane and 3,3,3-trifluoropropylmethyldichlorosilane or 1H, 1H,2H,2H-perfluorodecylmethyldichlorosilane via co-hydrolysis in ether. Polymerization was carried out as in the previous case.

The European patent publication EP 0563902 by Dow Corning[12] describes a method for preparation of block co-copolymers from $D_3$ and $D_3$-type cyclic monomers having 1H,1H,2H,2H-perfluoroalkylmethylsiloxane groups and/or vinylmethylsiloxane groups. See Scheme 2.

U.S. Pat. No. 4,814,418[13] describes a similar procedure, but instead of sequential addition of monomers, they add them simultaneously, resulting a non-block copolymer. The patent covers the use of cyclic trimers of $\{[F(CF_2)_aC_2H_4](CH_3)SiO\}_3$ and $\{[H(CF_2)_aC_2H_4](CH_3)SiO\}_3$ (a=1 . . . 16) with or without $D_x$(x=3 . . . 6) and/or $D_x^{Me vi}$(x=3 . . . 6, Vi=alkenyl group). The patent also claims higher molecular weight polymers by use of a phase transfer catalyst/initiator combination instead of initiator alone. Phase transfer catalyst is a quaternary ammonium or phosphonium salt and can be presented by the formulas $R_4N^+X^-$ or $R_4P^+X^-$, where R is alkyl, cycloalkyl or phenyl group and $X^-$ is $Cl^-$ or $Br^-$.

Scheme 1

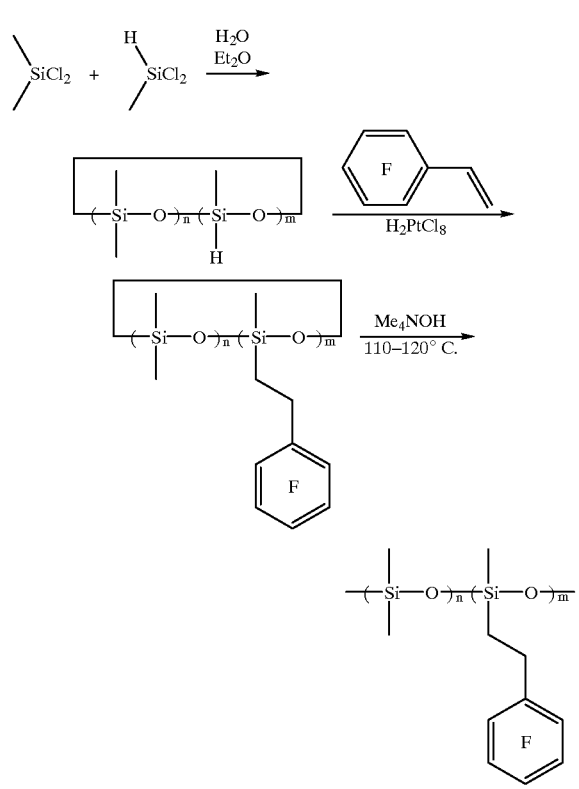

Scheme 2

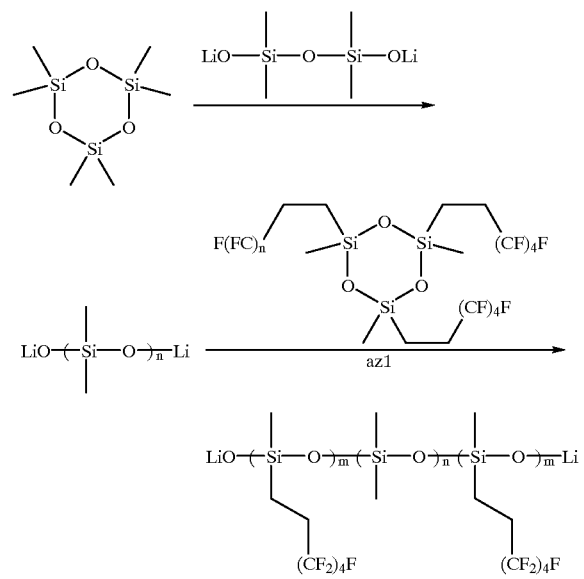

OBJECTS AND SUMMARY OF THE INVENTION

The aim of this invention is to provide novel fluoroalkyl-substituted cyclotrisiloxanes and novel polymers made thereof, either homopolymers made by anionic or cationic polymerization, or block copolymers made by anionic polymerization of said fluoroalkylsubstituted cyclotrisiloxanes.

Thus, according to one aspect, this invention concerns novel fluoroalkyl substituted cyclotrisiloxane of the formula (Ia) and (Ib)

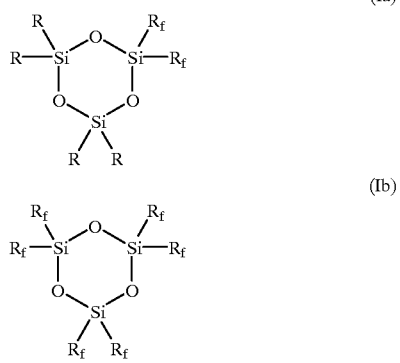

wherein R is a lower alkyl of 1 to 4 carbon atoms and $R_f$ has the formula $(CH_2)_2-(CR'_2)_n-CR'_3$, wherein all or some of the R' substituents are F, the remaining R' substituents being H, and n is an integer varying from 0 to 8, provided that $R_f$ cannot be $(CH_2)_2-CF_3$ in the compound of formula (Ib).

According to another aspect, this invention concerns a method for the preparation of a homopolymer, wherein said compound of formula (Ia) or (Ib) is subjected to anionic or cationic polymerisation in bulk or in a suitable solvent to give said homopolymer.

According to a further aspect, the invention concerns a method for the preparation of a block copolymer or random copolymer, wherein at least two of the compounds of formula (Ia), (Ib) and a cyclosiloxane (II),

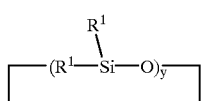

wherein y is 3, 4 or 5 and all or some of the $R^1$ substituents are alkyl of 1 to 4 carbon atoms, vinyl or phenyl, or wherein one $R^1$ is $R_f$ as defined before and the remaining $R^1$ substituents are alkyl of 1 to 4 C-atoms, vinyl or phenyl, are subjected to anionic or cationic polymerisation to give said block or random copolymer.

The invention concerns also the novel homopolymers, block copolymers and random copolymers.

DETAILED DESCRIPTION OF THE INVENTION

The most preferable compounds of formula Ia and Ib are those where each of the R' substituents in $(CH_2)_2-(CR'_2)_n-CR'_3$ ($R_f$) is F.

The polymerization can be carried out either in bulk or in a suitable solvent.

The cationic polymerization is preferably initiated by trifluoromethane sulfonic acid (triflic acid).

The anionic polymerization is preferably initiated by a lithium containing base, for example dilithium diphenylsilanolate or dilithium tetramethyldisiloxanolate.

The compounds Ia, Ib and II can be polymerized in any order with respect to each other. They can also be mixed with each other before the initiation of the polymerization.

The invention will be described more in detail in The Experimental section in the following non-limiting examples.

Experimental

Spectroscopic Analysis $^1H$, $^{13}C$, $^{19}F$ and $^{29}Si$ NMR spectra were obtained on a Bruker AMX-500 MHz spectrometer. Forty percent w/v solutions in acetone-$d_6$ were used to obtain the spectra. $^{13}C$ and $^{19}F$ NMR spectra were obtained with broad band proton decoupling. An inverse gate decoupling pulse sequence with a 60 sec delay was used to acquire $^{29}Si$ NMR spectra. Tetramethylsilane (TMS) was used as an internal standard for $^1H$, $^{13}C$, $^{19}F$ and $^{29}Si$ NMR spectra, and $CFCl_3$ for $^{19}F$ spectra. IR spectra of neat films on NaCl plates were recorded on a Perkin Elmer Spectrum 2000 FT-IR spectrometer.

EXAMPLE 1

Preparation of 1,1-bis(1'H,1'H,2'H,2'H-perfluorooctyl)3,3,5,5-tetramethylcyclotrisiloxane a) Bis(1'H,1'H,2'H,2'H-perfluorooctyl)dichlorosilane Dichlorosilane (5.2 mL, 63 mmol), 1H,1H,2H-perfluoro-1-octene (27.7 mL, 126 mmol), 3 drops of 10% $H_2PtCl_6$ in THF/MeOH solution and 100 μL Pt/divinyltetramethyldisiloxane complex in toluene were placed into Ace pressure tube for 24 h. Distillation gave 13.0 g desired product, bp 96° C./0.2 mm. Yield 27.5%. $^1H$ NMR δ:1.66(m, 4H), 2.47(m, 4H). $^{13}C$ NMR δ: 11.04, 25.61(t, J=24 Hz), 106–123(m). $^{19}F$ NMR δ: –122.55(m, 4F), –119.46(br s, 4F), –119.09(br s, 4F), –1 18.07(br s, 4F), –111.89(p, 4F, J=15 Hz), –77.63(t, 6F, J=10 Hz). $^{29}Si$ NMR δ: 32.63.IR v: 2956, 2910, 2877, 1444, 1410, 1364, 1319, 1296, 1237,1202, 1146, 1121, 1073, 1019, 902, 812, 708, 649, 566, 533 cm$^{-1}$.

b) 1,1-Bis(1'H,1'H,2'H,2'H-perfluorooctyl)-3,3,5,5-tetramethylcyclotrisiloxane

Bis(1'H,1'H,2'H,2'H-Perfluorooctyl)dichlorosilane from step a) (20.0 g, 25 mmol) in 15 mL $Et_2O$ and tetramethyldisiloxanediol $^{14}$(4.19 g, 25 mmol) in 15 mL $Et_2O$ were simultaneously dropped into solution of $Et_3N$ (8.0 mL, 57 mmol) and 100 mL $Et_2O$ in 1 h. After filtration the solution was washed with water, dried over $MgSO_4$ and solvents were removed by evaporation. Fractional distillation gave 11.33 g (50.7% yield), bp 113° C./0.2 mm, mp 56° C. The reaction was cared out at room temperature. $^1H$ NMR δ: 0.21(s, 12H), 1.01(m, 4H), 2.29(m, 4H). $^{13}C$ NMR δ: 0.68, 5,98, 25.51(t, $J_{C-F}$=23 Hz), 106–123(m). $^{19}F$ NMR δ: –127.05(s, 4F), –124.21(s, 4F), –123.56(s, 4F), –122.53(s, 4F), –117.00(t, 4F, J=16 Hz), –82.16(t, 6F, J=10 Hz). $^{29}Si$ NMR δ: –13.35(1Si), –7.08(2Si). IR v: 2969, 2947, 2913, 1445, 1367, 1316, 1260, 1247, 1212, 1185, 1145, 1067, 1020, 808, 735, 691, 648, 605, 566, 528 cm$^{-1}$.

EXAMPLE 2

Anionic polymerization of 1,1-bis(1'H,1'H,2'H,2'H-perfluorooctyl)-3,3,5,5 -tetramethylcyclotrisiloxane.

Initiator for Anionic Polymerization

Dilithium diphenylsilanolate was prepared by treatment of diphenylsilanediol with n-butyl lithium in THF. Styrene was used as an indicator.[2] Tetramethyldisiloxanediol can be used instead of diphenylsilanediol in order to enhance initiator's solubility in low temperature polymerizations Monomer (1,1-bis(1'H,1'H,2'H,2'H-perfluorooctyl)-3,3,5,5-tetramethyl-cyclotrisiloxane) (2.0 g, 2.3 mmol), initiator (159 vL, 40 vmol) were allowed to react in 0.6 mL THF at RT for 2.5 h. Polymer was endcapped with trimethylchlorosilane and precipitated three times from CFCl$_3$ with hexanes/acetone solution. After drying under vacuum, 1.95 g (98% yield) was obtained. T$_g$=−64° C. $^1$H NMR δ: 0.19(m, 12H), 0.94(m, 4H), 2.23(m, 4H). $^{13}$C NMR δ: 1.10, 6.02, 25.67(t, J=23 Hz), 102–125(m). $^{19}$F NMR δ: −126.45(4F), −123.34(4F), −122.99 (4), −121.96(4F), −116.29.(4F), −81.47(6F). $^{29}$Si NMR δ: −26.35, −26.21, −25.85, −25.80, −25.76, −20.84, −20.337, −20.25, −20.02, −19.97, −19.77, −19.62, −19.60, −19.54 −19.45, −19.21, −18.84. IR ν: 2966, 2912, 1444, 1423, 1420, 1363, 1352, 1317, 1296, 1264, 1240, 1210, 1197, 1167, 1146, 11.119, 1104, 1073, 1018, 950, 905, 844, 807, 747, 738, 707, 651, 566, 532 cm$^{-1}$.

EXAMPLE 3

Cationic polymerization of 1,1-bis(1'H,1'H,2'H,2'H-perfluorooctyl)-3,3,5,5 -tetramethylcyclotrisiloxane Monomer (1,1-bis(1'H,1'H,2'H,2'H-perfluorooctyl)-3,3,5,5-tetramethylcyclotrisiloxane) (2.0 g, 2.3 mmol) and CFCl$_3$ (1 mL) were sealed into 10 mL test tube equipped with magnetic stir bar and rubber septum. System was cooled to −9 ° C. and 2 μL of solution consisting of 50 μL triflic acid in 2 mL toluene was injected. Polymerization was allowed to proceed for 1 hour, after which polymer was precipitated as above yielding 1.7 g (85%). Polymer properties were as above.

EXAMPLE 4

Hexakis(1'H,1'H,2'H,2'H-perfluorooctyl) cyclotrisiloxane.

A solution of bis(1,1,2,2-tetrahydroperfluorooctyl) dichlorosilane, (10.6 g, 13.4 mmol) and 25 mL dry CHCl$_3$ were placed in a 50 mL rb flask equipped with a 10 mL dropping funnel. DMSO, (2,10 g, 26.9 mmol) in 6 mL CHCl$_3$ was dropped into the solution in 30 min at rt, and the reaction was allowed to proceed for 5 h. The flask was then cooled to 0° C., and the upper layer was decanted out. [15,16]The lower layer was washed once with 30 mL CHCl$_3$. The $^{29}$Si NMR showed 81% D$_3$ and 19% D$_4$-type monomer composition of the crude reaction product. It was distilled through a short path distillation apparatus. Hexakis(1'H,1'H, 2'H,2'H-perfluorooctyl)-cyclotrisiloxane (6.00 g, yield 61%), bp 200° C./0.01 mm was collected. $^1$H NMR δ: 1.19 (m, 8H), 2.37 (m, 8H). $^{13}$C NMR δ: 6.51, 25.84(t, J$_{C-F}$=24 Hz), 107.61–122.55(m). $^{19}$F NMR δ: −126.16(s, 8F), −123.02(s, 8F), −122.64(s, 8F), −121.61(s, 8F), −115.95(t, 8H, J=13 Hz), −81.31(t, 12F, J=11Hz). $^{29}$Si NMR δ: −10.27 (s, 3Si). IR ν: 2981, 2950, 2913, 2871, 1443, 1422, 1353, 1318, 1298, 1238, 1192, 1144, 1074, 1012, 952, 909, 897, 811, 777, 747, 727, 708, 651, 566, 528 cm$^{-1}$.

EXAMPLE 5

Poly[bis(1'H,1'H,2'H,2'H-perfluorooctyl)siloxane-co-dimethylsiloxane]

Hexakis(1'H,1'H,2'H,2'H-perfluorooctyl)cyclotrisiloxane (0.78 g, 0.35 mmol), octa-methylcyclotetrasiloxane (1.05 g, 3.6 mmol) and triflic acid (40 μL, 0.24 mmol) were placed into a test tube equipped with a Teflon covered magnetic stirring bar and a rubber septum. The system was heated to 100° C. and allowed to react for 7 h. The tube and its contents were cooled to RT. Hexamethyldisilazane (100 μL, 0.47 mmol) was added to neutralize the acid. The crude polymer solution was cloudy. It was washed twice with acetone, perfluorohexane, toluene and methanol, and dried in vacuum for 6 h. In this way, clear, colorless material, M$_w$/M$_n$=20,010/13,190, T$_g$=−123° C., 0.50 g (27%) was obtained. $^1$H NMR δ: 0.11 (s, 24 H), 1.01 (m, 1.33 H), 2.25 (m, 1.33 H). $^{13}$C NMR δ: 1.35, 5.96, 25.41 (m), 106.78–121.76(m). $^{19}$F NMR δ: −126.37 (2 F), −123.17 (2 F), −122.98 (2 F), −121.96 (2 F), −116.12 (2 F), −81.29 (3 F). $^{29}$Si NMR δ: −26.66 (6.5 Si), −24.82 ( 4.5 Si), −24.18 (10.0 Si), −23.52 (5.4 Si), −21.99 (100.0 Si), −21.74 (7.9 Si), −21.56 (8.3 Si), −21.14 (7.7 Si), −20.67 (2.6 Si), −20.38 (6.4 Si), −20.18 (9.2 Si), −19.31 (3.4 Si), −18.71.(7.4 Si), −18.30 (1.4 Si), −4.76 (1.9 Si). IR ν: 2964, 2908, 1262, 1240, 1210, 1146, 1096, 1020, 865, 802, 746, 707. TGA (in N$_2$): Polymer is stable to 250° C., 90% is left at 345° C. At 430 ° C., 50% of the material is left. Above 500° C., 32% residue remains.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

1. Kuo, C. -M.; Saam, J. C.; Taylor, R. B., Polymer Int., (1994), 33, 187.
2. Battjes, K. P.; Kuo, C. -H., Miller, R. L.; Saam, J. C., Macromolecules, (1995) 28, 790.
3. Tarrant, P. T.; Dyckes, G. W.; Dunmire, R; Butler, G. B., J. Am. Chem. Soc., (1957) 79, 6536.
4. Petrov, A. D.; Ponomarenko, V. A.; Odabashyan, G. V., Izv. Akad., Nauk. SSSR, (1959), 443.
5. Petrov, A. D.; Ponomarenko, V. A.; Odabashyan, G. V., Izv. Akad., Nauk. SSSR, (1962), 174.
6. Out, G. J. J., Klok, H. -A., Schwegler, L., Frey, H., Möller, M., Macromol. Chem.Phys., (1995)196,185.
7. Geyer, A. M.; Haszeldine, R. N.; Leedham, K.; Marklow, R. J., J. Chem. Soc., (1957), 4472.
8. McBee, E. T.; Roberts, C. W.; Judd, G. F.; Chao, T. S., J. Am. Chem. Soc., (1955) 77, 1292.
9. Haszeldine, R. N., Brit. 895, 592, May 2, 1962.
10. Boutevin, B.; Pietrasanta, V.; Youssef, B., J. Fluor. Chem., (1986) 31, 57.
11. Nagase, Y.; Ochiai, J.; Matsui, K., Polymer, (1988) 29, 740.
12. Kobayashi, H., EP 0 563 902 A1, Mar. 30, 1993.
13. Miyake, H.; Shin-ya, S.; Furukawa, Y., U.S. Pat. No. 4,814,418, Mar. 21, 1989.
14. Harris, G. I., J. Chem. Soc. 1963, 5978.
15. Lu, P., Paulasaari, J. K., Weber, W. P., Organometallics (1996) 15, 4649.
16. Goossens, J. C., French Patent 1,456,981, Oct. 1, 1964, CA: 67:54259 (1967).

What is claimed is:

1. A fluoroalkyl substituted cyclotrisiloxane of the formula (Ia) and (Ib)

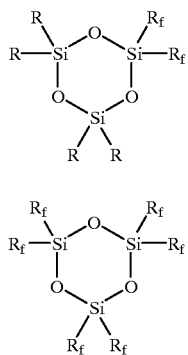

(Ia)

(Ib)

wherein R is a lower alkyl of 1 to 4 carbon atoms and $R_f$ has the formula $(CH_2)_2$—$(CR'_2)_n$—$CR'_3$, wherein all or some of the R' substituents are F, the remaining R' substituents being H, and n is an integer varying from 0 to 8, provided that $R_f$ cannot be $(CH_2)_2$—$CF_3$ in the compound of formula (Ib).

2. The compound according to claim 1 wherein each of tie R'-substituents is F.

3. The compound according to claim 1 wherein each of the R'-substituents is F, R is methyl and n is 5.

4. A method for the preparation of a homopolymer of formula (IIa) or (IIb), wherein a compound of formula (Ia) or (Ib)

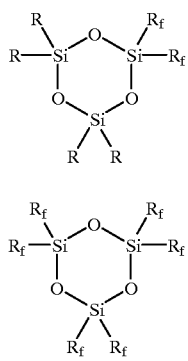

(Ia)

(Ib)

wherein R is a lower alkyl of 1 to 4 carbon atoms and $R_f$ has the formula $(CH_2)_2$—$(CR'_2)_n$—$CR'_3$, wherein all or some of the R' substituents are F, the remaining R' substituents being H, and n is an integer varying from 0 to 8, provided that $R_f$ cannot be $(CH_2)_2$—$CF_3$ in the compound of formula (Ib), is subjected to anionic or cationic polymerisation in bulk or a suitable solvent to give said homopolymer.

5. The method according to claim 4 wherein the polymerization is a cationic polymerization initiated by trifluoromethane sulfonic acid (triflic acid).

6. The method according to claim 4 wherein the polymerization is an anionic polymerization initiated by a lithium containing base.

7. The method according to claim 6, wherein the lithium containing base is dilithium diphenylsilanolate or dilithium tetramethyldisiloxanolate.

8. A homopolymer as prepared by claim 4.

9. A method for the preparation of a block copolymer or random copolymer, wherein at least two of the compounds of formula (Ia), (Ib) and a cyclosiloxane of formula (II),

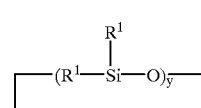

(II)

wherein y is 3, 4 or 5 and all or some of the $R^1$ substituents are allyl of 1 to 4 carbon atoms, vinyl or phenyl, or wherein one $R^1$ is $R_f$ as defined before and the remaining $R^1$ substituents are alkyl of 1 to 4 C-atoms, vinyl or phenyl, are subjected to anionic or cationic polymerisation to give said block or random copolymer.

10. The method according to claim 9 wherein the anionic polymerization is initiated by a lithium containing base.

11. The method according to claim 10, wherein the lithium containing base is dilithium diphenylsilanolate or dilithium tetramethyldisiloxanolate.

12. A block copolymer or random copolymer as prepared by claim 9.

* * * * *

UNITED STATES PATENT AND TRADEMARK OFFICE
CERTIFICATE OF CORRECTION

PATENT NO.   : 6,291,623 B1
DATED        : September 18, 2001
INVENTOR(S)  : Jyri Kalevi Paulasaari and William P. Weber It is certified that error appears in the above-identified patent and that said Letters Patent is hereby corrected as shown below:

Column 1,
Lines 25-30, please rewrite as follows:
-- propene.[3] The reaction has also been applied to the preparation of bis (trifluoropropyl) dichlorosilane using dichlorosilane instead of methyldichlorosilane. Unlike non-fluorinated alkenes (ethene, propene) which give good yields between 60 and 79%[4], 3,3,3-trifluoropropene gives only low yields, 26...36% in preparation of disubstituted silicon.[5] Bis(1H, --
Line 35, please rewrite as follows -- rosilane and 1H, 1H, 2H-perfluorohexane.[6] High yields --

Column 2,
Scheme 2, lines 43-59, rewrite a portion of the synthesis as follows:

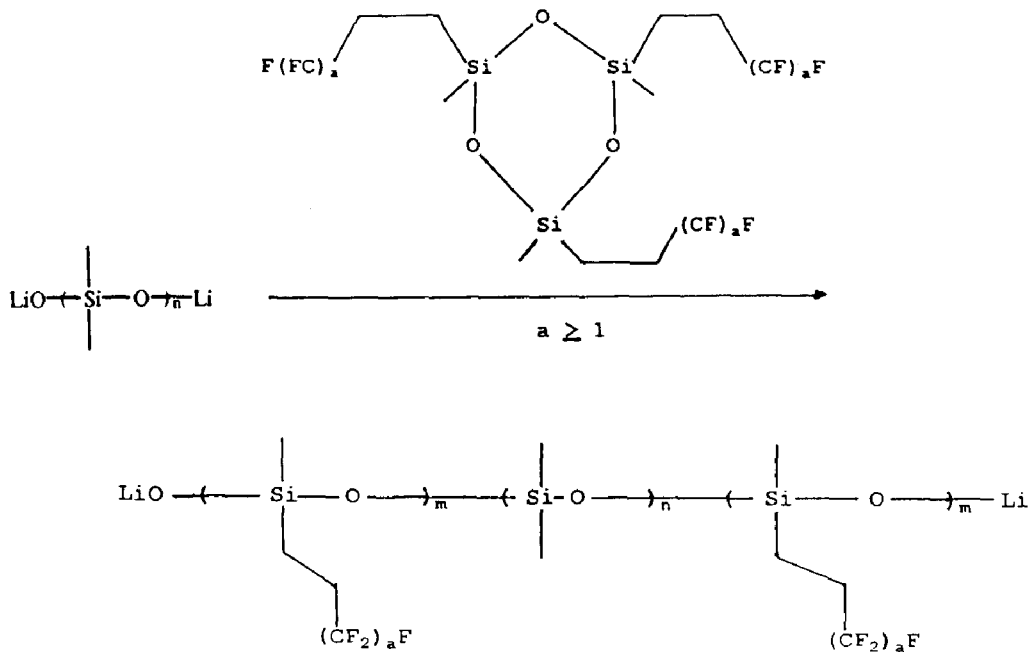

UNITED STATES PATENT AND TRADEMARK OFFICE
CERTIFICATE OF CORRECTION

PATENT NO.    : 6,291,623 B1
DATED         : September 18, 2001
INVENTOR(S)   : Jyri Kalevi Paulasaari and William P. Weber It is certified that error appears in the above-identified patent and that said Letters Patent is hereby corrected as shown below:

<u>Column 5,</u>
Line 6, rewrite as follows -- (159 µL, 40 µmol) were allowed to react in 0.6 mL THF at --

Signed and Sealed this

Sixteenth Day of July, 2002

*Attest:*

JAMES E. ROGAN
*Attesting Officer*     *Director of the United States Patent and Trademark Office*